US009476827B2

United States Patent
Ozanam et al.

(10) Patent No.: US 9,476,827 B2
(45) Date of Patent: Oct. 25, 2016

(54) SYSTEM AND METHOD OF MULTITECHNIQUE IMAGING FOR THE CHEMICAL BIOLOGICAL OR BIOCHEMICAL ANALYSIS OF A SAMPLE

(75) Inventors: François Ozanam, Leuville-sur-Orge (FR); Jean-Noël Chazalviel, Antibes (FR); Rabah Boukherroub, Villeneuve d'Ascq (FR); Elisabeth Anne-Gabrielle Galopin, Clamart (FR); Anne Chantal Gouget-Laemmel, Garches (FR); Sabine Szunerits, Villeneuve d'Ascq (FR); Larbi Touahir, Croix (FR)

(73) Assignees: Ecole Polytechnique, Palaiseau (FR); Centre National De La Recherche Scientifique-CNRS, Paris (FR); Universite Des Sciences Et Technologies De Lille 1, Villeneuve d'Ascq (FR)

( * ) Notice: Subject to any disclaimer, the term of this patent is extended or adjusted under 35 U.S.C. 154(b) by 672 days.

(21) Appl. No.: 13/991,798

(22) PCT Filed: Dec. 7, 2011

(86) PCT No.: PCT/FR2011/052886
§ 371 (c)(1),
(2), (4) Date: Aug. 12, 2013

(87) PCT Pub. No.: WO2012/076810
PCT Pub. Date: Jun. 14, 2012

(65) Prior Publication Data
US 2013/0314528 A1  Nov. 28, 2013

(30) Foreign Application Priority Data
Dec. 7, 2010  (FR) ...................................... 10 60195

(51) Int. Cl.
*G01N 21/27* (2006.01)
*G01N 21/552* (2014.01)
*G01N 21/64* (2006.01)
*G02B 21/08* (2006.01)
(Continued)

(52) U.S. Cl.
CPC ............ *G01N 21/27* (2013.01); *G01N 21/554* (2013.01); *G01N 21/6456* (2013.01);
(Continued)

(58) Field of Classification Search
CPC ............ G01N 2021/6463; G01N 2021/6471; G01N 2021/6493; G01N 21/27; G01N 21/554; G01N 21/6456; G01N 21/6458; G01N 21/65; G02B 21/082; G02B 21/16
USPC .......................................................... 348/79
See application file for complete search history.

(56) References Cited

U.S. PATENT DOCUMENTS 3,229,564 A  1/1966  Meltzer
4,072,426 A  2/1978  Horn
(Continued)

FOREIGN PATENT DOCUMENTS

WO   WO 2007/070382 A2   6/2007

*Primary Examiner* — Anner Holder
(74) *Attorney, Agent, or Firm* — Arent Fox LLP

(57) ABSTRACT

The invention substantially relates to an imaging system for the chemical, biological or biochemical analysis of a sample (10), comprising
 a device (40) for holding the sample (10),
 a device (20) for optical detection,
 a lighting device (30), liable to emit a monochromatic light beam, and
 a wide aperture objective (f1),
It is substantially characterized in that the objective (f1) is configured for, downstream of the sample (10):
 focusing the excitation light beam reflected at a point (C) located in the focal plane (FF) of said objective (f1), and
 transforming the retransmitted or scattered light beam into a quasi-parallel beam,
and in that the system further comprises a device (70) for selectively blocking the collected light beam by said objective (f1).

14 Claims, 1 Drawing Sheet

Figure 1:
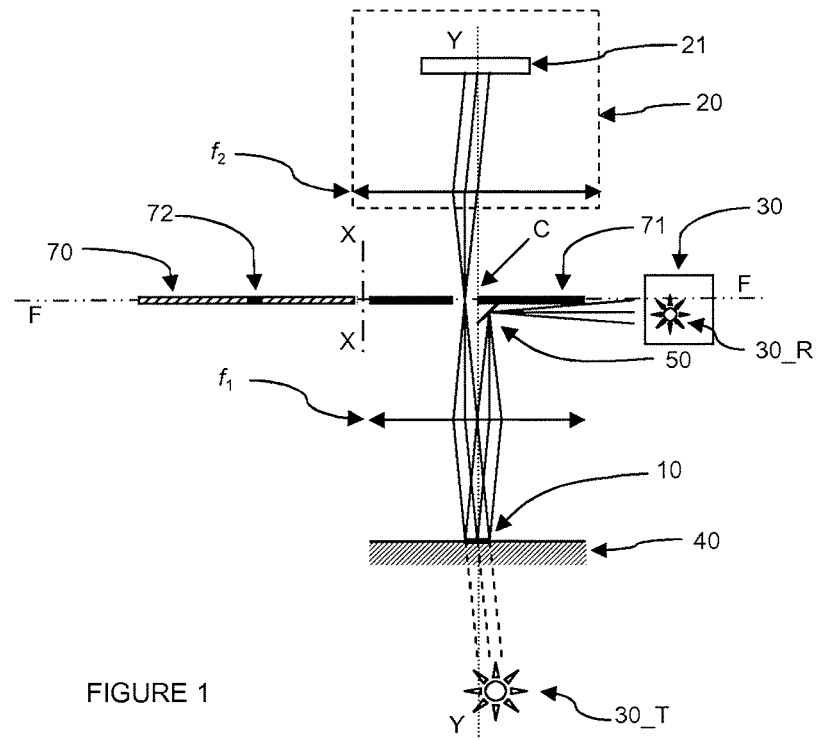

(51) Int. Cl.
*G02B 21/16* (2006.01)
*G01N 21/65* (2006.01)

(52) U.S. Cl.
CPC ............ *G01N 21/65* (2013.01); *G02B 21/082* (2013.01); *G02B 21/16* (2013.01); *G01N 21/6458* (2013.01); *G01N 2021/6463* (2013.01); *G01N 2021/6471* (2013.01); *G01N 2021/6493* (2013.01)

(56) References Cited

U.S. PATENT DOCUMENTS

| | | | |
|---|---|---|---|
| 6,548,796 B1 * | 4/2003 | Silvermintz | G02B 21/0024 250/201.3 |
| 2004/0090621 A1 | 5/2004 | Bennett et al. | |
| 2006/0238745 A1 | 10/2006 | Hashimoto et al. | |

* cited by examiner

SYSTEM AND METHOD OF MULTITECHNIQUE IMAGING FOR THE CHEMICAL BIOLOGICAL OR BIOCHEMICAL ANALYSIS OF A SAMPLE

CROSS-REFERENCE TO RELATED APPLICATIONS

This application is a National Stage entry of International Application PCT/FR2011/052886 filed Dec. 7, 2011, which claims priority of French Patent Application No. 1060195 filed Dec. 7, 2010, the disclosure of these prior applications are hereby incorporated in their entirety by reference.

The present invention relates to the field of imaging for the chemical, biological and biochemical analysis of a sample.

It is a particular implementation in the context of biosensors, where the use of substrates having metal deposits in the form of nanostructures makes it possible to obtain spectacular increases in sensitivity. The samples generally come in the form of "spots" or (micro) drops of known substances (or to be analyzed) deposited on holders such as microscope slides and on which optical analyses are carried out by making an image of the slide by one or the other of the techniques mentioned herebelow, possibly after or while placing the sample in contact with a substance to be analyzed (or of known composition, respectively).

More precisely, the invention relates to according to a first of its purposes an imaging system for the chemical, biological or biochemical analysis of a sample, the system comprising
  a device for holding the sample,
  an optical detection device
  a lighting device, liable to emit a monochromatic light beam, and
  a wide aperture objective Such a microscope system is well known to the skilled person.

In recent years, numerous developments have been carried out in microscopy as regards imaging techniques having a contrast revealing certain properties of the imaged object, particularly in reflectance/transmittance UV/visible spectroscopy otherwise called LSPR for "Localized Surface Plasmon Resonance" or surface plasmon resonance, in fluorescence (especially MEF for "Metal-Enhanced Fluorescence"), as well as Raman scattering (or SERS for "Surface-Enhanced Raman Scattering").

The present invention advantageously uses some of these techniques in the field of biosensors.

In fact, biosensors offer more efficient solutions than conventional tests on membranes, especially when they can be used in configurations allowing for a massively parallel measurement of several probe/target pairs on a same holder.

However, the broadband measurements of biomolecular interactions, particularly for proteins but also for molecules of lower molecular weight such as oligonucleotides, is an important issue in certain applications such as diagnostic or screening for the search of new drugs.

To measure these interactions, it is essential to be able to measure according to time the association/dissociation kinetics of probe/target pairs. The real-time measurement of these interactions is also necessary to have effective solutions for applications in the field of control (particularly when it consists of "flow" control, for example to control products at the output of production lines) or monitoring (for example the environmental detection of toxic markers). For these types of measurements, it is essential to measure according to time the events or association/dissociation kinetics of probe/target pairs, which depending on the case may be or may not be subject to a specific marking for example, with a fluorescent marker.

Among the currently available techniques, two types of detection provide effective solutions for the monitoring of molecular interactions in real-time: fluorescence and resonance of surface plasmons.

Currently available on the market are instruments based on one or the other of this type of detection that allow for real-time in situ monitoring of the association and/or dissociation of a couple of biomolecules (a probe attached to the surface of a solid holder and a target present in sample to be analyzed).

Fluorescence provides the best sensitivity, but has the disadvantage of having to mark targets or probes with fluorophore groups.

The advantage of surface plasmon resonance is that it is able to detect interactions between unmarked target and probe, but has a lower sensitivity. In its conventional version, the constraints pertaining to the excitation geometry make the imaging tricky. It may advantageously be used in imaging mode by exciting localized surface plasmon resonance (LSPR) in metal layers structured in the form of islets of nanometric dimensions. The analysis is then carried out by means of a simple spectroscopic analysis of the variation of the reflection or transmission of the layer at the contact of a sample.

When using probes marked with a fluorophore, an LSPR analysis conducted in parallel with the fluorescence analysis may be used to detect the presence of non-specific adsorption on the sensor, which, beyond a certain threshold, may conceal probes making the sensor practically insensitive. Such a control is essential to maintain performance in applications in the field of control and surveillance. When unmarked probes are used, the LSPR used on its own also has the disadvantage of not providing chemical discrimination.

That is why it is known that its coupling with a chemical identification technique without marking such as Raman scattering represents a major purpose.

However, these techniques have somewhat contradictory requirements.

For reflectance/transmittance spectroscopy, it is desirable to work in normal or near-normal incidence with a small angular aperture, and it is useful to be able to continuously vary the wavelength. In fact, in order to determine the conditions of measurement, it is required to be able to acquire a spectrum in the entire visible range and possibly UV and/or IR, at the risk of then fixing the latter once the conditions of measurement are defined.

For the fluorescence, for reasons of sensitivity, it is required to collect the light emitted over a solid angle that is as wide as possible, and the excitation must be monochromatic and intense such as to maximize the fluorescence signal.

For Raman scattering just as for fluorescence, the emitted light must be collected on an as wide as possible solid angle, the excitation must also be monochromatic and intense, however it is also necessary to analyze the distribution in wavelength of the light emitted by the sample and more specifically the changes in wavelength (Raman shifts) with respect to the excitation radiation. This usually leads to insert a dispersive device (such as for example a diffraction grating) between the sample and the detector, which is not compatible with the direct recording of an image. An alternative consists in using a holographic grating, or more generally a spatial filtering device, and then reconstruct images for each analyzed wavelength by means of programs for processing elaborate images.

At present, there is no solution that meets the requirements pertaining to all these techniques. Moreover, no solution seems a priori satisfactory for simply comparing Raman images resolved in wavelength with those provided by the other techniques.

In this context, the device according to the invention which further conforms to the preamble above, is substantially characterized in that the objective is configured for downstream of the sample:

focusing the excitation light beam reflected at a point (C) located in the focal plane of said objective, and transforming the retransmitted or scattered light beam into a quasi-parallel beam, and in that it further comprises a device for selectively blocking the collected light beam from the sample by said objective, preferably arranged in said focal plane; selectively allowing for the analysis of the sample based on two at least analysis techniques from the set comprising surface plasmon resonance, fluorescence, and Raman scattering as described later.

As defined by the present invention, upstream and downstream are defined with respect to the direction of the light beam from the source to the detector.

In one embodiment, the selective blocking device includes

A diaphragm configured to be placed in the focal plane of said objective around the focal point F, and A shutter configured to be placed at focal point C.

Preferably, the selective blocking device further comprises at least one filter from an assembly comprising a high-pass filter and a bandpass filter.

In one embodiment, the system further comprises, upstream of said objective, means for reflecting the light beam from said source of said beam towards the sample holding device.

Preferably, said reflecting means comprises a mirror arranged in the vicinity of the optical axis, or a semi-transparent mirror placed in the optical axis, oriented at 45°±2° with respect to the optical axis, and arranged such as to observe the sample in transmission or in reflection with a minimum shading.

Advantageously, the device for selectively blocking the collected light beam further comprises an electrical or mechanical switch, for selectively activating said diaphragm or said shutter.

In one embodiment, the lighting device comprises a white light source associated with a monochromator, and/or a source of monochromatic light, that is tunable or not.

In one embodiment, the lighting device comprises an assembly of at least one optical fiber and an assembly of at least one unit light source, possibly tunable, and wherein the input of at least one fiber is liable to be connected to at least one unit source.

In one embodiment, the input of at least one fiber is liable to be connected to a plurality of unit sources, the system further comprising a switch for connecting the input of the fiber to one of the unit sources in a relative movement between the input of the fiber and the unit source connected to the input of the latter.

In one embodiment, there is a plurality of monochromatic sources each connected to one or several fibers, the fibers from each unit source being mixed in input of a fiber beam whereof the output is used for the excitation of the sample. The switching between the sources can then be carried out without relative movement, by electrically activating the selected unit source, or by means of shutters placed at the output of each unit source. Such an embodiment may be advantageous when the unit sources are LEDs or non-tunable lasers.

According to another of its purposes, the invention also relates to a method for chemical, biological or biochemical analysis of a sample, in a system according to the invention, comprising steps consisting of:

illuminating a sample with a monochromatic light beam, and focusing the beam downstream of the sample by an objective at a point C located in the focal plane of said objective. The method is substantially characterized in that it further comprises steps consisting in:

selectively blocking said collected beam, acquiring several images by means of a camera of said sample based on the selective blocking.

In one embodiment, the method further comprises a step of superimposing said images.

In one embodiment, the method further comprises a step of filtering the light beam, downstream of the selective focusing.

In one embodiment, the method further comprises steps consisting in:

tuning the monochromatic light source of said light beam, and measuring different Raman shifts according to the selected tuned wavelength.

Thanks to the invention, it is possible to easily compare images recorded by two or three of the cited techniques, particularly by simple superposition, thanks to a joint optical column and CCD sensor for all these techniques, that is to say coupling the different techniques within a same apparatus, without moving the sample with respect to the optical axis.

Thanks to the invention, it is possible to carry out tests in order to obtain information of chemical or biochemical nature with or without marking the targets or probes, to correlate the information obtained by at least two independent techniques and carry out real-time performance controls of the tests of the holders used for the tests. These performances are obtained by allowing the coupling of different techniques within the same apparatus.

Thanks to the invention, it is possible to carry out the imaging of a centimetric area, with a resolution of the order of 10 µm, sufficient for imaging spots of a diameter of the order of 100 µm.

Thus, while the solutions of the prior art were interested in the fluorescence exaltation by coupling with localized surface plasmon resonance (LSPR), without associating the measurement of the two sizes, it is possible, as described here, to implement (without moving the sample) the detection of LSPR and the detection of the fluorescence exalted by the plasmon effect under identical conditions. Thanks to the invention, this association makes it possible to achieve interesting realizations for example for the control of the immobilization of unmarked probes before the detection of marked targets during an experiment, or the simultaneous detection of marked targets with low molecular weight and unmarked targets with high molecular weight during the same experiment.

The present invention also makes it possible to carry out a broadband measurement of real-time biomolecular interactions, a fundamental issue in certain fields of application such as diagnostic or screening for the research of new drugs. Likewise, the measurement of chemical recognition of specific targets in real time is also necessary to have effective solutions for applications in the field of control and surveillance.

Figure 2:
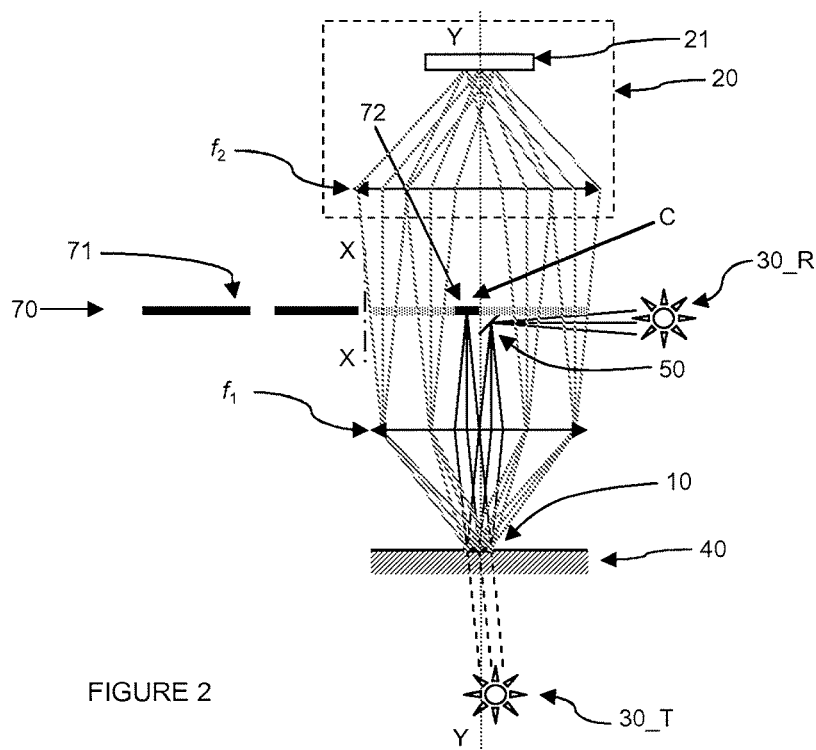

Other characteristics and advantages of the present invention will become more apparent upon reading the following description given by way of illustrative and non-limiting example and made with reference to the accompanying drawings in which:

FIG. 1 shows an embodiment of the system according to the invention in LSPR configuration, with a light source in reflectance and/or a light source in transmittance, and FIG. 2 illustrates an embodiment of the system according to the invention in MEF configuration, also with a light source in reflectance and/or a light source in transmittance.

One of the principles of the present solution is to implement a unique optical detection device 20 for a plurality of possible analysis techniques from among the set comprising LSPR, the MEF and SERS (see definitions above).

The optical detection device 20 comprises a lens or group of lenses f2 and a detector such as a CDD sensor 21 (or camera). The magnification of the optical system is determined once the dimensions of the CCD and area to be explored are fixed.

It is also provided an additional lens f1 (lens or group of lenses) described below and serving for shaping the collected light beam, from the sample 10 and incident on the detector 21.

For the group of f2 lenses, it is to be considered a zoom lens, which makes it possible to adapt upon request, the dimensions of the explored area. Alternatively, the zoom function can be ensured by the objective f1, but in this case, the distance between the point C and the objective must be adjusted, which is less advantageous. For a good measurement sensitivity, it is advantageous to use a CCD camera with adjustable integration time, such as to be able to adapt it according to the light intensity to be detected. For measurements with a very high sensitivity (which may be the case for the measurement of Raman scattering or fluorescence for certain samples) it may be advantageous to use a cooled CCD camera, such as to be able to use long measurement times for recording each image.

Whatever the chosen analysis technique for the present solution, the illumination of a sample 10 consists in a quasi-parallel incident light beam, of intensity as uniform as possible over the entire surface of the studied area. The wavelength of this lighting, monochromatic, may however be variable or not, and the beam can illuminate the sample according to two configurations, also called geometries:

A configuration of reflectance measurements, called front illumination, where the sample is directly illuminated by the incident light beam, from a lighting device 30_R and reflects the latter to an optical detection device 20;

A configuration of transmittance measurements, called rear illumination, where the sample is indirectly illuminated by the incident light beam, from a lighting device 30_T via a portion at least of the holding means 40 of the sample, and transmits it towards an optical detection device 20.

For fluorescence or Raman scattering, the lighting can be carried out by the front or the rear. However, a front illumination is slightly more favorable, as it results in substantially lower parasitic light (for example due to scatterings by defects or dust, or even fluorescence or Raman scattering of the substrate on which the analyzed sample is deposited and through which this sample is illuminated).

The quasi-parallel form of the incident light beam for the lighting of a sample 10 may be carried out as follows.

In configuration of reflectance measurements, the light beam is derived from the lighting device 30_R. It is then focused, for example by a lens, onto a slanted mirror 50, placed (in the detection column) at a few millimeters from the optical axis YY and the focal plane FF, in this case, higher than the objective f1, that is to say in the vicinity of the focal point C of the objective f1. For example, the mirror 50 may be a mirror of a diameter of 2 mm, whereof the center is located at 3±1 mm from the optical axis.

Thanks to this positioning, the objective f1 retransforms the beam into a quasi-parallel beam at the sample 10.

By way of alternative (not shown), a semi-transparent mirror may be placed in the optical axis YY, also close to the focal plane FF of the objective f1, that is to say, in the vicinity of the focal point C of the objective f1.

The first arrangement requires working outside the optical axis (more difficult adjustments, more significant optical aberrations), but the second one has the drawback of losing a factor T(1-T) on the collected intensity (T being the transmission coefficient of the semi-transparent mirror), which is preferable to be avoided in fluorescence and Raman scattering.

In the embodiment illustrated in FIG. 1, the optical axis, hence the optical column is vertical, the light beam from the lighting device 30_R is horizontal, such that the mirror 50 is slanted at around 45° (45°±2°). Preferably, the slanted mirror 50 is as small as possible (diameter of the order of 1 mm to a few mm), and the inclination of the beam with respect to the optical axis is as small as possible, considering the necessity of preventing the rays converging in C from intercepting said mirror 50.

In configuration of transmittance measurement, the light beam is derived from the lighting device 30_T. It is put in quasi-parallel shape by the non-represented optical and directed towards the sample through the rear, in near-normal incidence.

In another embodiment of transmittance measurements (not shown), it can be implemented a mirror slanted at about 45° (45°±2°) and placed on the optical axis upstream of the sample, and below it.

In order to obtain a (quasi)monochromatic light beam, the lighting device 30_R, 30_T may comprise a white light source (for example a xenon arc lamp, an arc lamp or incandescent lamp) associated with a monochromator, or a monochromatic light source (light-emitting diode, laser diode or laser), tunable or not.

In both cases, the shaping of the quasi-parallel beam can be carried out by injecting the light from the source into a fiber or a beam of optical fibers of medium aperture (advantageously less than or equal to 0.2) coupled with a lens.

It is worth noting that for all measurements (analysis techniques), in the case of an excitation illumination transmitted through optical fiber, the uniformity of the lighting of the area to be explored is based on the homogeneity of the angular distribution of the beam from the optical fiber. Any possible uniformities can be corrected either by a gradient filter or an appropriate holographic filter interposed at the collimating lens, or by digital correction at the image analysis, these two corrective techniques can also be combined. Finally, the parallel beam can be collimated in order to obtain an illumination on a non-circular area, for example square or rectangular.

By light source as defined by the present invention, is meant a unit light source, namely a plurality of unit light sources, each unit light source able to emit over a common monochromatic wavelength or according to a respective monochromatic wavelength.

The objective f1 comprises a lens or sets of lenses, of focal length f1, providing at the detector 21 a magnification f2/f1 of the order of 1 (advantageously comprised between 0.1 and 10). In order to meet fluorescence requirements, the aperture of said objective f1 is as large as possible (advantageously at least 1:1.4).

The objective f1 is configured in order to focus the excitation light beam downstream of the sample, at a point C located in the focal plane (in this case, higher) FF of said objective f1 (which in the case of a simple lens is located at distance f1 over this lens.)

The large aperture objective f1 allows for, upstream of the sample, to illuminate it according to a quasi-parallel beam of normal or near-normal incidence, and downstream of the sample, on the one hand, to focus the reflected beam at the point C located in the focal plane of said objective, and on the other hand to transform the scattered beam into a quasi-parallel beam, such that it may possibly be detected by the optical detection device 20 according to a large solid angle (for example, for a 1:1.4 aperture, half-angle at the top close to 20° and solid angle of 0.12 π steradians).

Thus, as shown on FIG. 2, the beam from the specular reflection is focused by the objective f1 at the point C downstream of the sample, whereas the scattered beam (re-emitted by the sample) is not focused but is transformed into a quasi-parallel beam.

It is worth noting that during the specular reflection, the light beam is reflected by the sample with a wavelength identical to that of the incident beam. During the scattering, for example in fluorescence or Raman scattering, the light beam is re-emitted or scattered by the sample based on a wavelength different from the incident wavelength (excluding Rayleigh scattering).

A selective blocking device 70 is advantageously placed in the focal plane of the collected light beam (by the objective f1).

This selective blocking device 70 makes it possible to selectively analyze the sample based on at least two analysis techniques from among the group comprising surface plasmon resonance, fluorescence and Raman scattering, as described later.

The device 70 for selectively blocking the light beam comprises, for example:

A diaphragm 71 configured to be placed in the focal plane of said objective around the focal point C, such as to block the unfocused portion of the beam so that only the focused portion is transmitted towards the detection device 20, and A shutter 72, preferably complementary to the diaphragm 71, configured to be placed at the focal point C, such as to create an opaque area on and around point C, such as to block the focused portion of the beam so that only the unfocused portion be transmitted to the detection device 20, so that the latter may detect based on a large solid angle.

The device 70 for selectively blocking the light beam may further comprise at least one filter (not shown) from among the assembly comprising a high-pass filter and a bandpass filter.

The high-pass filter is implemented for the detection of fluorescence, and the bandpass filter for the detection of Raman scattering.

Preferably, the bandpass filter is a narrow bandpass filter, which allows obtaining a good resolution for determining Raman shifts, and advantageously placed at the shutter. For this reason, a narrow-band interference filter can be used. Advantageously, the bandwidth of the filter is less than or equal to 3 nm. For example, the filter of a diameter of 50 mm reference 03 FIL 008 commercialized by Melles Griot, which has a bandwidth of 1 nm centered at a wavelength of 632.8 nm, allows for the measurement of Raman shifts with a resolution of 25 $cm^{-1}$.

For the measurement of fluorescence, it may also be advantageous to place at the shutter 72 a filter blocking the wavelength of the light used for the excitation, thus one protects oneself against parasitic radiation due to the scattering of the excitation light by the surface of the sample 10 or by the defects or dust of the optical system.

In order to optimize the detection sensitivity, it may be advantageous to use combinations of optical filters. For example, the rate of rejection of a bandpass filter can be increased for certain blocked wavelengths by superimposing a high-pass filter and/or a low-pass filter, or by superimposing a low-pass filter and a high-pass filter for limiting the detection band of the fluorescence in order to be better protected against parasitic signals.

According to various embodiments, it may be provided that the filter or filters be coupled to said shutter 72, and possibly secured to the movement of the latter. For example, it can be provided that the shutter 72 be movable in rotation and that a set of at least one filter be also movable in rotation, possibly secured to the movement of said shutter 72.

The diaphragm 71 and shutter 72 thus, allow to respectively select the type of analysis technique from among the assembly comprising surface plasmon resonance, fluorescence and Raman scattering.

The selective blocking of the light beam by the device 70 is implemented by switching between the diaphragm 71 and the shutter 72.

Switching between the diaphragm 71 and the shutter 72 may be implemented by a mechanical switch, for example, by rotational movement around an axis XX (FIG. 1), preferably parallel to the optical axis YY, thanks to a pivoting disk. Or it can also be provided a travelling movement, preferably in a plane parallel to the focal plane FF, for example thanks to a sliding pull-out.

With a mechanical switch, the disc or pull-out may possibly also have other optical functions (bright-field imaging: wide diaphragm, dark-field imaging: a cover of the area around the point C, but no filter). One can also provide an electrical switch by a liquid crystal shutter device or an electrochromic device.

Preferably, the assembly comprising device 70 for selectively blocking the light beam and the mirror 50 (when provided) is constructed in the form of a mechanically rigid block.

It is worth noting that the two assemblies (diaphragm possible filter and shutter 72 vs. slanted mirror 50) cannot be located, exactly and simultaneously, in the focal plane FF of the objective f1. In practice, a shift of a few millimeters is tolerable, considering the focal depth of the objective f1 and the diameter of the mirror 50, which may be slightly oversized.

Thus, thanks to the selective blocking of the light beam, it is possible to use one and the same detection device 20 for the different analysis techniques: plasmon resonance, fluorescence, and Raman.

Based on the chosen analysis technique, that is to say, based on the blocking of the focused portion or not of the light beam, it is sufficient to adapt the lighting device 30 to select a particular wavelength for lighting the sample 10.

The lighting device 30 is liable to emit a monochromatic light beam, variable or not.

For this purpose, the lighting device 30 may comprise an assembly of at least one optical fiber and an assembly of at least one unit light source.

It can be provided that at least one unit source is tunable, and/or that at least one unit source is a white source, the lighting device 30 thus further comprising a monochromator.

Several embodiments are possible. For example, the input of each fiber may be connected to a respective unit source or the input of a unique fiber is switched, moved, from unit source to unit source. Alternatively, it can be provided that the unique fiber be fixed and the unit sources be switched (moved) to the entry of the latter. As seen before, it can also be provided a fiber beam in which the input of at least two fibers is liable to be connected to a respective light source, the system further comprising an electrical or optical switch for selectively activating said light source.

Thus, the switching of the light source may be carried out either with movement by moving the end of an optical fiber (unique fiber whereof the entry is moved from one source to another, or fibers each connected to a respective source, the output of one of them being chosen (selected) to light the sample 10); or without movement for example by source with variable wavelength, or white source coupled to a monochromator.

The system operates as follows:

For a technical analysis of surface plasmon resonance, in LSPR configuration, the light beam transmitted (reflected) by the sample 10 is collected through the diaphragm 71 placed at the point of convergence C of the objective f1, the diaphragm making it possible to filter the unfocused portion of the beam at the output of the objective f1, such that only the focused portion of the light beam reaches the detection device 20.

For a measurement technique or fluorescence analysis (FEA) or Raman scattering (SERS), the light beam transmitted (reflected) by the sample 10 is blocked by the shutter 72 (preferably complementary to the diaphragm 71) the shutter 72 making it possible to filter the focused portion of the beam at the output of the objective f1 such that only the non-focused portion of the light beam reaches the detection device 20. Thus, the light is collected by the detector over a large solid angle.

For the realization of a standard Raman imaging, the need to analyze the light scattered inelastically by the monochromatic excitation in order to determine the Raman signatures allowing for molecular identification (Raman shifts) has led designers to insert a spectral analysis device (dispersive element and/or a combination of delaying elements) between the sample and the detector. This constraint makes it difficult to create a system allowing for the direct comparison with reflectivity measurements for the LSPR analysis.

In order to resolve this constraint, the present solution proposes on the other hand to achieve the detection of Raman scattering at a determined wavelength, and to carry out the measurement of Raman shifts by varying the excitation wavelength, which allows for a simple and direct comparison of the LSPR images, Raman and fluorescence, and seems completely innovative. Particularly, it is useful to be able to make such a comparison without processing the images, and by having the possibility to compare the images with different contrasts and recorded by different techniques pixel by pixel.

In addition, for a technique for measuring or analyzing Raman scattering according to the present solution, the light source is monochromatic and tunable such as to be able to measure different Raman shifts by selecting different wavelengths for the excitation. Thus, Raman images are directly recorded corresponding to the light scattered at the wavelength $\lambda\_det$ selected by the narrow filter used for the detection, for an excitation wavelength from the light source $\lambda\_exc$. The Raman shift is the same in all respects as the obtained image and its value $\Delta v$ (expressed in wave numbers) is given by the relation $\Delta v = (1/\lambda\_exc) - (1/\lambda\_det)$.

By successively recording images for different values of $\lambda\_exc$, one thus, obtains images for different Raman shifts directly and easily comparable with the images recorded by the other techniques.

The radiation being detected at a wavelength distinct to that of the excitation radiation, the retained principle further has the advantage of preventing any parasitic contribution due to the Rayleigh scattering of the sample 10 or the optical system.

Thus, for the measurement of Raman scattering, it is advantageous to use sources that are sufficiently intense and which have a precisely defined wavelength.

To this regard, lasers or laser diodes are used and preferred to light-emitting diodes.

For example, it may be provided as a source, a tunable solid laser (for example a laser of titanium type: sapphire, possibly equipped with a frequency doubler system depending on the field of wavelength required for the excitation) or a source based on an optical parametric oscillator (OPO).

These sources can be continuous light sources or pulses. When using a pulse source, it is advantageous to have a pulse duration higher than or equal to 100 fs such as to maintain the monochromatic character of the source, and the highest possible repetition rate. For example, commercial sources may be used based on OPO that provide illumination in the form of pulses of a few ns transporting tens of mJ with a repetition rate of 10 Hz or more; such sources provide high instantaneous power favorable to the observation of the Raman effect. However, in cases where it is sought to measure the presence or absence of a known Raman signal, it may be economical to not use a tunable excitation source and to only use one or two or a very small number of monochromatic sources (the presence of several sources advantageously makes it possible to provide reference measurements for which no Raman scattering is expected).

Thus, a spectroscopic measurement with high resolution and/or in a wide range of Raman shifts can be benefited from.

It is also worth noting, still for Raman scattering measurement, that to avoid the presence of parasitic radiation in the detected signal, it is advantageous to filter the excitation light beam by means of a (blocking) rejection filter whereof the stop band is centered on the wavelength selected for the detection. The width of this filter stop band determines the lowest Raman shifts that can be measured by the system. For example, this filter can be a holographic filter with high rejection power. For example, the filter of reference 53684 marketed by Oriel reduces the intensity of radiation at 632.8 nm by a factor higher than $10^6$, with a blocking band width of 28 nm and makes it possible to detect Raman shifts higher than 350 cm$^{-1}$. However, this filter being used in transmission on the excitation, it may be advantageous to use filters with less blocking power but having excellent transmission outside the blocking band such as to have a system that is more resistant to high excitation intensities. For example, the multilayer filter with continuous index variation of reference B46-566 marketed by Edmund Optics reduces the radiation intensity to 632.8 nm by a factor higher than $10^3$, with a blocking band width slightly lower than 32 nm, which makes it possible to detect Raman shifts higher than 400 $cm^{-1}$. Considering their high transmission outside the blocking band, it is possible to use two or several of these filters in series in order to increase the power of rejection. When the source is a laser or a laser source based on an OPO, the rejection filter is advantageously arranged at the source output.

The simple substitution of a set of filters and diaphragms inserted in the optical column at the focal plane of the objective f1 makes it possible to switch from the arrangement of reflectivity measurement to the arrangement of fluorescence measurement or Raman scattering.

The system can also allow keeping the basic imaging function (bright-field/dark-field) by adding an additional set of diaphragms. It makes it possible to carry out tests in the air or in contact with a liquid medium and in real-time in order to achieve kinetic measurements. The coupling of the different techniques within the same tests makes it possible to obtain information of chemical or biochemical nature with or without marking of targets or probes, to correlate the obtained information by at least two independent techniques and carry out performance controls of the tests in real-time of the holders used for the tests.

Hence, the system can implement a method of chemical, biological or biochemical analysis of a sample 10, wherein said sample is illuminated with a monochromatic light beam; several images of said sample are acquired by switching between two at least analysis techniques from among the set comprising surface plasmon resonance, fluorescence, and Raman scattering, and said images are superimposed.

For measurements of transmittance/reflectance UV-visible as for Raman scattering measurement, the necessary spectral analysis is carried out by recording several images corresponding to several excitation wavelengths. In this case a tunable source may be advantageous.

Thanks to the invention, it is possible to focus the transmitted or specularly reflected beam, such as to be able to either select it by making it pass through a diaphragm (reflectance/transmittance) or mask it by means of a shutter (fluorescence, Raman scattering), while retaining the possibility of imaging the studied surface. In order to conveniently compare the images recorded in the different modes, for the Raman analysis, neither the dispersive analysis device, nor the spatial filtering device are used on the detection system, on the contrary, solely the light emitted in a narrow band of wavelengths selected by a filter is detected.

Hence, it is possible thanks to the present solution to combine in a same apparatus the advantages of the detection/analysis modes by LSPR, SERS and fluorescence. This apparatus hence, makes it possible to acquire several superimposable images of a same sample with different types of contrast, which is particularly useful in the context of holders having a layer with high LSPR activity making it possible to exalt the two other physical effects and exceed the usual limitations associated with the chemical immobilization of probes. The combination of the apparatus, purpose of the present invention with such holders makes high performance chemical and biochemical tests possible, with real-time multi-technique detection and under usual testing conditions in physiological medium.

The invention is not limited to the aforementioned embodiments. It can be applied in other contexts. For example, it is possible to perform massively parallel biological recognition tests in a format distinct from that of biochips by using the possibility to encode particles of the size of the order of 100 μm by imparting them with a particular optical structure. These encoded particles may be generated in large numbers at a low cost with more than $10^{\wedge}6$ distinct codes. These codes are read by measuring the reflectivity spectrum of the particle. In order to carry out tests, the same probe is grafted onto all the particles of the same code, and then all the particles are placed in contact with a sample to be analyzed containing targets marked by a fluophore. The particles are then dispersed (by deposit then evaporation) at the surface of a microscope slide, and molecular recognition is analyzed by measuring the reflectivity spectrum and fluorescence of each particle under the optical microscope. By providing a solution to carry out these measurements in imaging mode for a large number of particles simultaneously, the present invention provides a solution liable to impart these types of tests with the broadband it could not have had until now.

The invention claimed is:

1. An imaging system for the chemical, biological or biochemical analysis of a sample (10), comprising
    a device (40) for holding the sample (10),
    a device (20) for optical detection,
    a lighting device (30), liable to emit a monochromatic light beam, and
    a wide aperture objective (f1),
characterized in that the objective (f1) is configured for, downstream of the sample (10):
    focusing the reflected excitation light beam at a point (C) located in the focal plane (FF) of said objective (f1), and
    transforming the retransmitted or scattered light beam into a quasi-parallel beam,
and in that the system further comprises a device (70) for selectively blocking the collected light beam by said objective (f1).

2. The system according to claim 1, wherein the device (70) comprises
    A diaphragm (71) configured to be placed in the focal plane of said objective around the focal point (C),
    A shutter (72) configured to be placed at the focal point (C).

3. The system according to claim 2, wherein the device (70) further comprises at least one filter from among a set comprising a high-pass filter and a bandpass filter.

4. The system according to claim 1, further comprising, upstream of said objective, means for reflecting the light beam from the source of said beam towards the sample holding device (40).

5. The system according to claim 4, wherein said reflection means comprise a mirror (50) arranged in the vicinity of the optical axis (YY), or a semi-transparent mirror placed in the optical axis (YY), oriented at 45°+/−2° with respect to the optical axis, and arranged such as to observe the sample (10) in transmission or reflection.

6. The system according to claim 2, wherein the device (70) for selectively blocking the collected light beam further comprises an electrical or mechanical switch, for selectively activating said diaphragm (71) or said shutter (72).

7. The system according to claim 1, wherein the lighting device (30) comprises a white light source associated with a monochromator and/or a monochromatic light source, that is tunable or not.

8. The system according to claim 1, wherein the lighting device (30) comprises a set of at least one optical fiber and a set of at least one unit light source, possibly tunable, and wherein the input of at least one fiber is liable to be connected to at least one unitary source.

9. The system according to claim 8, wherein the input of at least one fiber is liable to be connected to several unitary sources, the system further comprising a switch for connecting the fiber input to one of the unitary sources in a relative movement between the fiber input and the unitary source connected to the input thereof.

10. The system according to claim 1, further comprising a fiber bundle wherein the input of at least two fibers is liable to be connected to a respective light source, the system further comprising an electrical or optical switch for selectively activating said light source.

11. A method of chemical, biological or biochemical analysis of a sample on a sample holder, comprising the steps of:
- illuminating a sample (10) by a monochromatic light beam,
- focusing the excitation beam downstream of the sample (10) by an objective (f1) at a point (C) located in a focal plane (FF) of said objective (f1),
- selectively blocking the collected beam, and
- acquiring several images by a camera (20) of said sample (10) based on the selective blocking.

12. The method according to claim 11, further comprising a step of comparing said images.

13. The method according to claim 11, further comprising a step of filtering the light beam downstream of the focusing of the excitation beam.

14. The method according to claim 11, further comprising the steps in
- tuning the monochromatic light source of said light beam, and
- measuring different Raman shifts according to the selected tuned wave length.

* * * * *